United States Patent
Giannini

[11] Patent Number: 5,360,450
[45] Date of Patent: Nov. 1, 1994

[54] PROSTHESIS FOR THE CORRECTION OF FLATFOOT

[75] Inventor: Sandro Giannini, Viareggio, Italy

[73] Assignee: Howmedica International Div.ne Pfizer Italiana S.p.A., Latina, Italy

[21] Appl. No.: 28,184

[22] Filed: Mar. 9, 1993

[30] Foreign Application Priority Data

Mar. 9, 1992 [IT] Italy ................. LU92U/1

[51] Int. Cl.⁵ .................................. A61F 2/42
[52] U.S. Cl. ........................... 623/21; 623/16; 606/77
[58] Field of Search ........... 623/21, 18, 17, 16; 606/63, 77

[56] References Cited

U.S. PATENT DOCUMENTS

| | | | |
|---|---|---|---|
| 4,450,591 | 5/1984 | Rappaport. | |
| 4,973,333 | 11/1990 | Treharne | 606/77 |
| 5,007,930 | 4/1991 | Delcommune et al. | 623/66 |
| 5,084,050 | 1/1992 | Draenert | 606/77 |
| 5,207,712 | 5/1993 | Cohen | 623/21 |

FOREIGN PATENT DOCUMENTS

| | | | |
|---|---|---|---|
| 0011528 | 5/1980 | European Pat. Off. | 606/77 |
| 0401844 | 12/1990 | European Pat. Off. . | |
| 2543821 | 10/1984 | France . | |
| 2615726 | 12/1988 | France | 623/18 |
| 2680968 | 3/1993 | France | 623/21 |
| 3509417 | 9/1986 | Germany . | |
| 4000112 | 7/1991 | Germany . | |
| 0293485 | 9/1991 | Germany | 606/63 |
| 8803781 | 6/1988 | WIPO | 623/17 |

*Primary Examiner*—David H. Willse
*Attorney, Agent, or Firm*—Oblon, Spivak, McClelland, Maier & Neustadt

[57] ABSTRACT

A prosthesis for the correction of a flatfoot condition of a patient, which is designed for insertion inside a recess or tarsal sinus defined between a first bone or astragalus and a second bone or calcaneus; wherein the prosthesis is made of bioreabsorbable material. The prosthesis has a club-shaped body or a slightly conical body.

9 Claims, 1 Drawing Sheet

PROSTHESIS FOR THE CORRECTION OF FLATFOOT

BACKGROUND OF THE INVENTION

1. Field of the Invention

The present invention relates to a prosthesis for the correction of flatfoot.

2. Discussion of the Background

The deformity commonly known as flatfoot is caused by excessive movement of the astragalus in relation to the calcaneus, and is corrected surgically by inserting, inside a recess defined between the above two bones, a prosthesis which provides for limiting movement of the astragalus in relation to the calcaneus. Currently used prostheses comprise a cylindrical body made of stainless steel or plastic, i.e. a material extraneous to the body and which in time may result in problems to the patient. During articulation of the foot bones, in fact, friction occurs between the bones and the prosthesis resulting in obvious discomfort to the patient as well as wear on the bones, so that a second surgical operation is required to remove the prosthesis. Moreover, the majority of patients having recourse to such a prosthesis are children and adolescents for whom a second operation is particularly distressing.

SUMMARY OF THE INVENTION

It is an object of the present invention to provide a prosthesis for the correction of flatfoot, designed to overcome the aforementioned drawback, and which, more specifically, does not require a surgical operation for its removal.

According to the present invention, there is provided a prosthesis for the correction of flatfoot, designed for insertion inside a recess or tarsal sinus defined between a first bone or astragalus and a second bone or calcaneus; characterized by the fact that it is made of bioreabsorbable material.

BRIEF DESCRIPTION OF THE DRAWINGS

A preferred, non-limiting embodiment of the present invention will be described by way of example with reference to the accompanying drawings, in which.

DESCRIPTION OF THE PREFERRED EMBODIMENT

Figure 1:
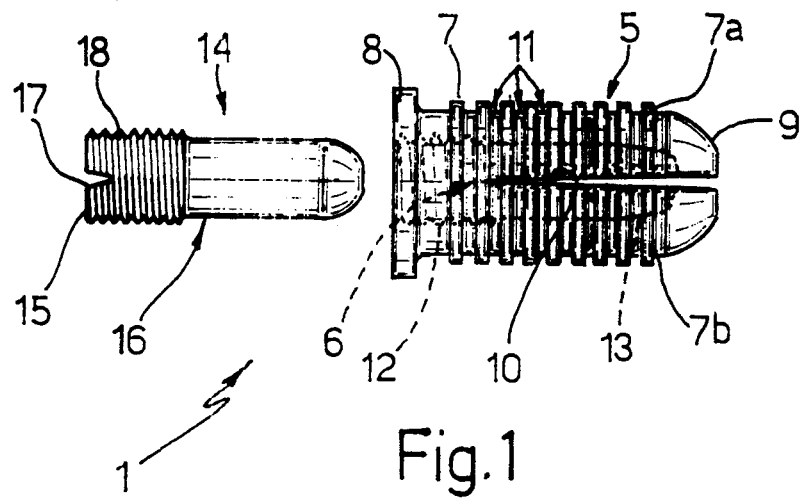
FIG. 1 shows an exploded side view of a prosthesis in accordance with the teachings of the present invention.
Figure 2:
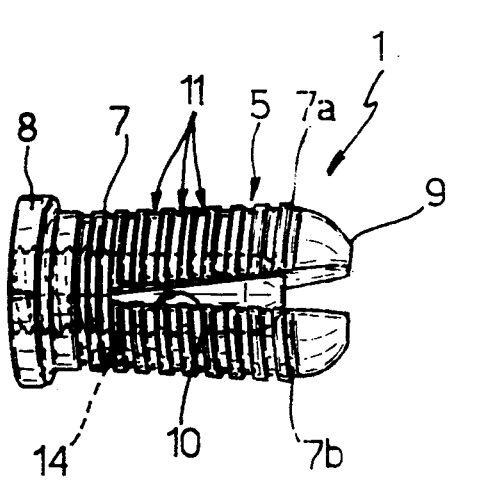
FIG. 2 shows a side view of the FIG. 1 prosthesis assembled for use.
Figure 4:
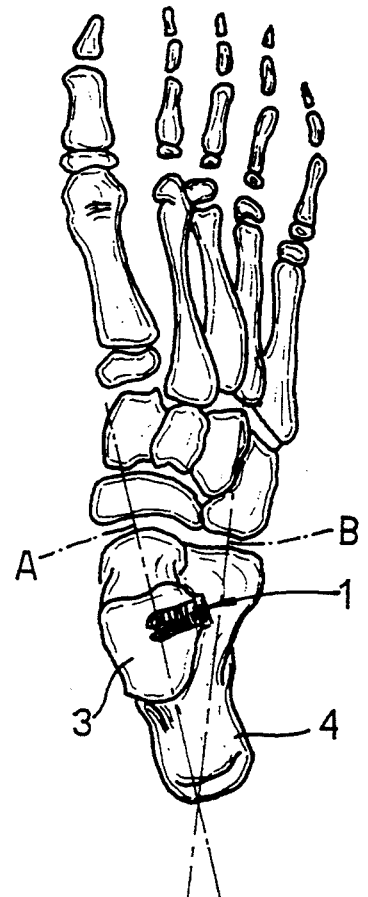
FIGS. 3 and 4 show respective side and underside views of the bone structure of a foot featuring the FIG. 2 prosthesis.
Figure 3:
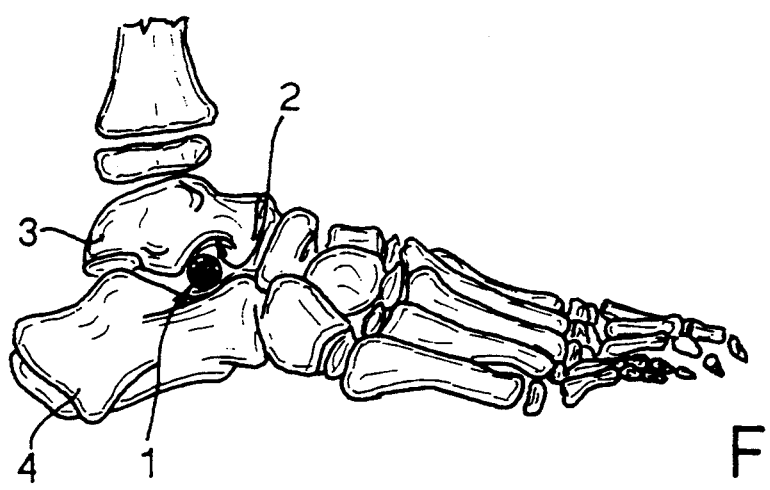

Number 1 in FIGS. 1 and 2 indicates a prosthesis for correcting the deformity known as flatfoot. As shown in FIGS. 3 and 4, this is achieved by inserting the prosthesis 1 surgically inside a recess 2 or tarsal sinus defined between a first bone 3 or astragalus and a second bone 4 or calcaneus, the function of prosthesis 1 consisting in limiting movement of astragalus 3 in relation to calcaneus 4, the excessive movement of which is known to be the cause of the deformity.

In the FIG. 1 embodiment, prosthesis 1 comprises a first substantially cylindrical body 5 having an axial dead hole 6 as shown by the dotted line, a cylindrical wall 7, an outer annular flange 8 at a first axial end of wall 7, and a substantially semispherical head 9 closing a second axial end of wall 7. Between flange 8 and head 9, the outer surface of wall 7 presents a number of annular grooves 11, the functions of which are described later on. Hole 6 is defined by a threaded cylindrical portion 12 close to flange 8, and by a slightly conical portion 13 decreasing in diameter from portion 12 to head 9. Body 5 presents a longitudinal incision 10 formed through head 9 and along wall 7 substantially as far as threaded portion 12 of hole 6, and which defines two wings 7a and 7b.

As shown in FIGS. 1 and 2, prosthesis 1 comprises a second cylindrical body 14 constituting a screw by virtue of presenting a head 15, and, in this case, a partially threaded shank 16. Head 15 is equal in diameter to shank 16, and presents a diametrical slot 17 for receiving the tip of a tool such as an ordinary screwdriver. Shank 16 is equal in diameter to portion 12 of hole 6, and presents a threaded portion 18 close to head 15, and a semispherical free end.

In actual use, body 5 is first inserted inside recess 2; body 14 is then inserted inside body 5; and, using a tool, shank 16 is screwed inside hole 6. By virtue of incision 10 and the difference in diameter of shank 16 and portion 13 of hole 6, shank 16, when screwed inside hole 6, causes wings 7a and 7b to flex outwards, and is screwed inside hole 6 until wings 7a and 7b are so parted as to contact astragalus 3 and calcaneus 4 and achieve a predetermined position of axis A of astragalus 3 in relation to axis B of calcaneus 4. Annular grooves 11 define small spaces, for the growth of fibrous tissue, between prosthesis 1 and bones 3 and 4.

Prosthesis 1 is made of bioreabsorbable material, such as poly-DL-lactic acid, poly-L-lactic acid, or other polymers, and, according to laboratory tests, undergoes initial structural changes, while at the same time maintaining its shape, roughly six months after insertion, presents initial fractures after about a year, and is totally reabsorbed by the organism by the third year. As the time lapse for correcting the deformity is less than that required for reabsorbing the prosthesis, the bioreabsorbable material employed provides for a prosthesis designed to effectively correct the deformity and which is then reabsorbed by the organism.

The advantages of the present invention will be clear from the foregoing description.

In particular, the prosthesis according to the present invention, by virtue of being made of bioreabsorbable material, provides for eliminating the problems posed by known prostheses, which, being made of plastic or stainless steel, i.e. of material extraneous to the organism, must necessarily be removed surgically.

To those skilled in the art it will be clear that changes may be made to prosthesis 1 as described and illustrated herein without, however, departing from the scope of the present invention.

In particular, the prosthesis may consist of a single, solid, slightly conical or club-shaped body, similar to prosthesis 1 in FIG. 2.

I claim:

1. A prosthesis for correction of a flatfoot condition, designed for insertion inside a tarsal sinus defined between an astragalus bone and the calcaneous, which comprises:

a first cylindrical body having a deformable wall wherein said body is formed of a bioreabsorbable polymeric material and sized to be axially inserted into said tarsal sinus, said first body having an axial hole defined by said deformable wall, and a second substantially cylindrical body formed of said bioreabsorbable polymeric material and sized to be axially inserted into said hole to deform said wall as to increase the outer diameter thereof, such that the prosthesis is adjusted according to the size of said tarsal sinus when the prosthesis is surgically inserted into said tarsal sinus to achieve a given position of a longitudinal axis of the astragalus bone in relation to a longitudinal axis of the calcaneus.

2. A prosthesis as claimed in claim 1, wherein said first and second body are made of poly-DL-lactic acid.

3. A prosthesis as claimed in claim 1, wherein said bodies are made of poly-DL-lactic acid.

4. A prosthesis as claimed in claim 1, wherein said first body comprises one of slightly conical body and a club-shaped body.

5. A prosthesis as claimed in claim 1, wherein said hole comprises a partially threaded axial dead hole, and said first body is provided with an axial incision defining two deformable wings; and said second body is provided with a partially threaded shank which is screwed inside said hole of said first body for deforming and parting said wings in such a manner as to bring them into contact with the astragalus bone and the calcaneus.

6. A prosthesis as claimed in claim 5, wherein said wall of said first body is cylindrical, and said first body includes an outer annular flange at a first axial end of said wall, and a head closing a second axial end of said wall, said head being substantially semispherical.

7. A prosthesis as claimed in claim 6, wherein an outer surface of said wall has a plurality of annular grooves which, in use, define spaces for the growth of fibrous tissue.

8. A prosthesis as claimed in claim 7, wherein said hole is defined by a threaded cylindrical portion and by a slightly conical portion decreasing in diameter from said threaded portion to said head; said axial incision being formed through said head and along said wall substantially as far as said threaded portion.

9. A prosthesis as claimed in claim 8, wherein said second body comprises a head for receiving the tip of a tool; said shank has the same diameter as said threaded portion of said hole; and said shank has a threaded portion and a substantially semispherical free end.

* * * * *